(12) United States Patent
Jablonski et al.

(10) Patent No.: US 9,910,037 B2
(45) Date of Patent: Mar. 6, 2018

(54) CONJUGATION OF MULTIPLE VANCOMYCIN MOLECULES ON A POLYVINYL ALCOHOL BACKBONE FOR THE CAPTURE OF MICROORGANISMS

(71) Applicant: Iris International, Inc., Chatsworth, CA (US)

(72) Inventors: Edward Jablonski, Escondido, CA (US); Carl Hulle, Encinitas, CA (US)

(73) Assignee: Iris International, Inc., Chatsworth, CA (US)

( * ) Notice: Subject to any disclaimer, the term of this patent is extended or adjusted under 35 U.S.C. 154(b) by 339 days.

(21) Appl. No.: 14/776,476

(22) PCT Filed: Mar. 13, 2014

(86) PCT No.: PCT/US2014/026614
§ 371 (c)(1),
(2) Date: Sep. 14, 2015

(87) PCT Pub. No.: WO2014/151885
PCT Pub. Date: Sep. 25, 2014

(65) Prior Publication Data
US 2016/0041166 A1 Feb. 11, 2016

Related U.S. Application Data

(60) Provisional application No. 61/802,011, filed on Mar. 15, 2013.

(51) Int. Cl.
*A61K 9/00* (2006.01)
*G01N 33/569* (2006.01)
*C12Q 1/04* (2006.01)
*G01N 33/543* (2006.01)
*C08F 116/06* (2006.01)

(52) U.S. Cl.
CPC ...... *G01N 33/56938* (2013.01); *C08F 116/06* (2013.01); *C12Q 1/04* (2013.01); *G01N 33/54326* (2013.01); *G01N 33/56911* (2013.01)

(58) Field of Classification Search
CPC .................................................. G01N 33/56938
See application file for complete search history.

(56) References Cited

U.S. PATENT DOCUMENTS

2006/0292555 A1 12/2006 Xu et al.
2013/0004651 A1* 1/2013 Fu-Giles .............. A61K 9/0051
427/2.26

FOREIGN PATENT DOCUMENTS

WO  2007/016556 A1  2/2007

OTHER PUBLICATIONS

International Search Report and Written Opinion dated Jul. 28, 2014 for PCT Patent Application No. PCT/US2014/026614, 13 pages.
Kakinoki et al. "Synthesis and Evaluation of Water-Soluble Poly-(vinyl-alcohol)-paclitaxel Conjugate as a Macromolecular Prodrug," Biol. Pharm. Bull, May 2008, vol. 31, No. 5, pp. 963-969.
Lin et al. "Affinity Capture Using Vanomycin-Bound Magnetic Nanoparticles for the MALDI-MS Analysis of Bacteria," Anal. Chem., 2005, vol. 77, pp. 1753-1760.
Rao et al. "Tight Binding of a Dimeric Derivative of Vancomycin with Dimeric L-Lys-D-Ala-D-Ala," J. Am. Chem. Soc., 1997, vol. 119, pp. 10286-10290.

* cited by examiner

*Primary Examiner* — Paul Dickinson
(74) *Attorney, Agent, or Firm* — Kilpatrick Townsend & Stockton LLP

(57) ABSTRACT

The present disclosure relates to compositions, methods, and kits for the rapid detection, separation and/or isolation of microorganisms. Specifically, the disclosure relates to compositions, methods, and kits for using vancomycin—PVA backbone complexes to capture and/or concentrate microorganisms in an aqueous sample, such as gram positive and/or gram negative bacteria in solution.

24 Claims, No Drawings

CONJUGATION OF MULTIPLE VANCOMYCIN MOLECULES ON A POLYVINYL ALCOHOL BACKBONE FOR THE CAPTURE OF MICROORGANISMS

CROSS-REFERENCES TO RELATED APPLICATIONS

This application is a US National Phase of PCT Application No. PCT/US2014/026614, filed on Mar. 13, 2014, which claims priority to U.S. Provisional Patent Application No. 61/802,011, filed Mar. 15, 2013 and entitled "Conjugation of Multiple Vancomycin Molecules on a Polyvinyl Alcohol Backbone for the Capture of Microorganisms," the disclosures of which are herein incorporated by reference in their entirety for all purposes.

FIELD OF THE INVENTION

The present disclosure relates to compositions, methods, and kits for the rapid detection, separation and/or isolation of microorganisms. Specifically, the disclosure relates to compositions, methods, and kits for using vancomycin-PVA backbone complexes to capture and/or concentrate microorganisms in an aqueous sample, such as gram positive and/or gram negative bacteria in solution.

BACKGROUND

Infectious diseases are one of the world's most pressing health challenges and the development of strategies capable of quickly identifying infections presents a difficult challenge because most of the diagnostic applications currently employed are slow, expensive, and are not practical for point-of-care or field applications.

Microorganisms such as bacteria and viruses in biological samples are hard to detect at low concentrations and usually require long induction or incubation times before further analysis can be performed. Currently, the identification of microorganisms in biological samples is a time-consuming process. For bacterial detection, body fluid samples must be incubated for long periods of time before any bacterial cultures can be positively identified. Methods that can detect bacteria at ultralow concentrations without time-consuming incubation or amplification processes thus have certain advantages in clinical diagnosis, food safety, biodefense, and/or environmental monitoring applications.

Currently, the identification of bacteria in aqueous samples such as urine is a time-consuming process. Exemplary urine samples must be incubated for days before positive identification of any bacterial cultures can be microorganisms such as bacteria and viruses are hard to detect at low concentrations and usually require long induction or incubation times before further analysis can be performed. For bacterial detection, body fluid samples must be incubated for tong periods of time before any bacterial cultures can be positively identified. Methods that can detect bacteria at ultralow concentrations without time-consuming incubation or amplification processes thus have certain advantages in clinical diagnosis, food safety, biodefense, and/or environmental monitoring applications.

SUMMARY OF THE INVENTION

In one aspect, the instant disclosure is directed to a novel approach which uses PVA-vancomycin-conjugates to capture and detect microorganisms and/or pathogens such as Gram-positive or negative bacteria at very low concentrations. The compositions and method of this disclosure, may accordingly be used to expedite the identification of pathogens (viruses, bacteria, and fungi) by providing specific and efficient methods for microbial separation and/or detection.

This invention is useful in minimizing the time needed to positively identify the presence of bacteria in urine samples to a near "real-time" event. This invention identifies the specific ligands which attract and immoblize bacteria on a solid support matrix, This solid support matrix, in turn, can be concentrated (thus concentrating the microbes such as bacteria) leading to positive and rapid identification of bacteria within a short time after obtaining the sample.

In one aspect, the present disclosure relates to compositions comprising vanco-PVA coupled to a microsphere solid support, as well as kits comprising the microspheres, and methods of their use for the detection, affinity separation, enrichment, and/or reducing the concentration of microorganisms, for example, pathogens, in a sample. The microspheres or microsphere solid support may include functionalized protein microspheres, or functionalized magnetic particles, where the functional groups are capable of binding to said microorganisms via ligand-receptor, antibody-antigen, ionic, or metal-ligand interaction.

In one aspect, the present disclosure provides method and compositions for the capture of microorganisms such as gram positive bacteria with a vancomycin-PVA conjugate immobilized on a solid support. In some aspects, the solid supports for use in the compositions and methods of this disclosure are beads or particles, which can include, for example, microspheres or nanoparticles. In some aspects, the beads such as microspheres or nanoparticles may be magnetic.

In one aspect, the present disclosure provides a synthetic polymer of the general formula (I):

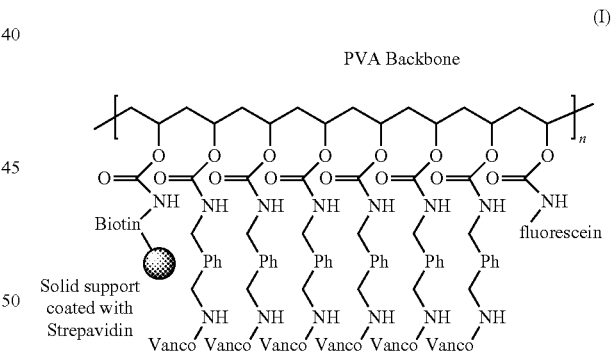

(I)

wherein n is 10 to 100,
where the synthetic polymer comprises repeating monomer units of polyvinyl alcohol wherein each hydroxyl group is covalently bound to a molecule of carbonyldiimidazole, wherein a first population of the monomeric units each comprises a linker covalently bound to the carbonyldiimidazole and a solid support, and wherein a second population of the monomeric units each comprises activated vancomycin, and wherein optionally a third population of the monomeric units each comprises a fluorescent molecule.

In one embodiment, the polymer includes more of the second monomeric units than of the first monomeric units. In one embodiment, the polymer includes more of the second monomeric units than of the third monomeric units.

In one embodiment, the linker is biotin. In one embodiment, the activated vancomycin is bound to the second population of the monomeric units through para-xylene diamine. In one embodiment, the fluorescent molecule is 5-aminoacetamido) fluorescein. In one embodiment, the synthesis of the polymer includes at least a ten-fold excess of the second monomeric units. In one embodiment, the solid support comprises magnetized particles. In one embodiment, the magnetized particles comprise Streptavidin particles.

In another aspect, the present disclosure provides a method for capturing microorganisms in a test sample comprising: a) adding a synthetic polymer comprising repeating monomer units of polyvinyl alcohol wherein each hydroxyl group is covalently bound to a molecule of carbonyldiimidazole, wherein a first population of the monomeric units each comprises a linker covalently bound to the carbonyldiimidazole and a solid support, and wherein a second population of the monomeric units each comprises activated vancomycin, and wherein optionally a third population of the monomeric units each comprises a fluorescent molecule to a solution comprising the microorganisms; b) agitating the mixture from step a) followed by incubation; c) applying a magnetic field to the mixture from step b); d) removing the liquid from step c); e) transferring the polymer from step d) to agar plates to allow any colony forming units to proliferated; and f) visually inspecting the agar plates from step e) for the presence of any colony forming units. In one embodiment, the microorganisms are grain positive bacteria. In one embodiment, the microorganisms are gram negative bacteria. In one embodiment, the microorganisms are selected from *Staphylococcus epidermidis* and *Streptococcus gallolyticus*. In one embodiment, the polymer includes more of the second monomeric units than of the first monomeric units. In one embodiment, the polymer includes more of the second monomeric units than of the third monomeric units. In one embodiment, the linker is biotin. In one embodiment, the activated vancomycin is bound to the second population of the monomeric units through para-xylene diamine. In one embodiment, the fluorescent molecule is 5-(aminoacetamido) fluorescein. In one embodiment, the polymer includes at least a ten-fold excess of the second monomeric units. In one embodiment, the solid support comprises magnetized particles. In one embodiment, the magnetized particles comprise Streptavidin particles.

In one aspect, a process for preparing a synthetic polymer of general formula (I) comprising the steps:

(I)

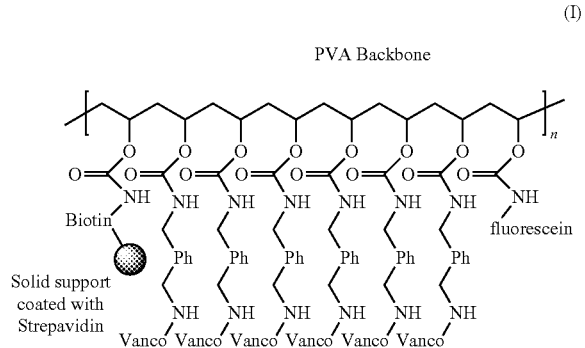

wherein n is 10 to 100, a) reacting vancomycin with para-xylene diamine to give the compound of formula (II):

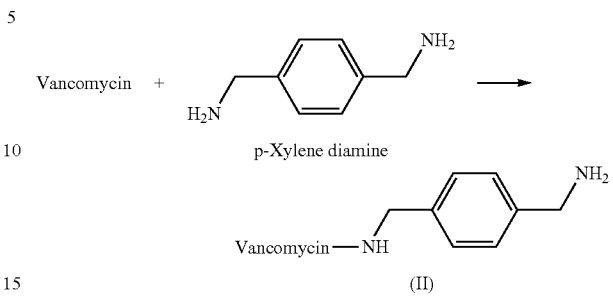

b) reacting polyvinyl alcohol with a molar excess of carbonyldiimidazole to give the compound of formula (III):

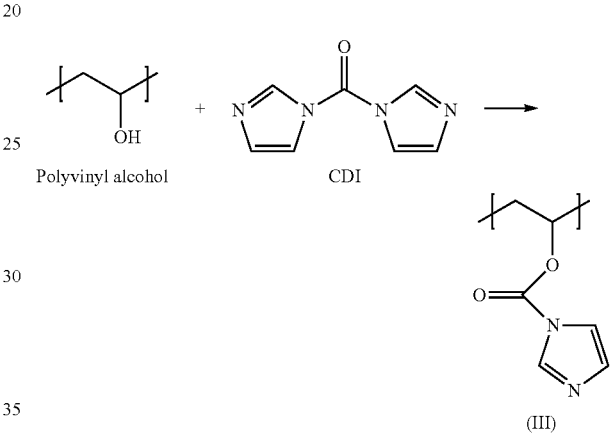

c) reacting the compound of formula (II) from step a), the compound of formula (III) from step b), a linker, and optionally, a fluorescent molecule to give a compound of formula (IV); and

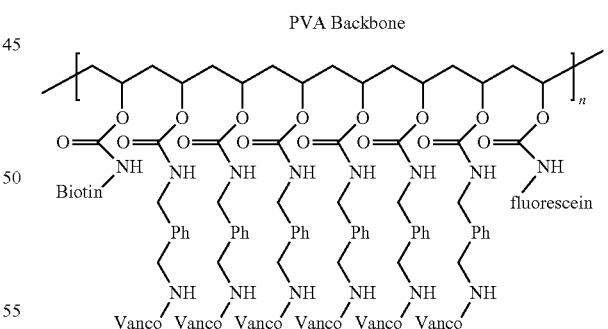

d) reacting the compound of formula (IV) from step c) with a solid support to produce synthetic polymer (I). In one embodiment, the carbonyldiimidazole is used in a molar excess from about 5 to about 15. In one embodiment, the linker is biotin. In one embodiment, the fluorescent molecule is 5-(aminoacetamido) fluorescein. In one embodiment, the solid support comprises magnetized particles. In one embodiment, the magnetized particles comprise streptavidin particles. In one embodiment, the vanco PVA-species complexes are separated aggregation of the vanco-PVA-species complexes under a magnetic field. In one embodiment, the complex comprises an affinity molecule selected from the group consisting of: a receptor, a ligand, an antibody, a hormone, RNA, DNA, PNA or nucleotide derivatives or analogs, or wherein the affinity molecule is biotin, or wherein the affinity molecule is an avidin or streptavidin. In one embodiment, the PVA backbone is conjugated to primary amine containing vancomycin produced by diaminoxylene (DAX) using HBTU chemistry. In one embodiment, the PVA-backbone is conjugated to avidin. In one embodiment, the PVA-backbone is conjugated to fluorescene. In one embodiment, the PVA-backbone is conjugated to polymyxin B; antilipid A; antigen; antiEcoli (pAb); lysozyme; deactivated lysozyme; anti-FLIC; cecropin; or bactenecin. In one embodiment, the sample is a liquid selected from blood, serum, plasma, spinal fluid, synovial fluid, saliva, urine, semen, cell and/or tissue homogenates. In one embodiment, the sample contains a species of bacterium. In one embodiment, the species is a gram-positive bacterium in one embodiment, the species is a gram-negative bacterium in one embodiment, the bacterium is *Staphylococcus*.

In one aspect, a composition for detecting a species in a sample, comprising the polymer of claim 1 is provided. In one aspect, a composition for concentrating or depleting a species in a sample, comprising the polymer of claim 1 is provided. In one aspect, a kit comprising the polymer of claim 1 and instructions for use is provided.

In another aspect, compositions comprising PVA-vancomycin fluorescene biotin conjugates are also provided. In another embodiment, the PVA complex comprises vancomycin.

Kits comprising one or more of the disclosed PVA vancomycin complexes are also provided.

DETAILED DESCRIPTION OF THE INVENTION

Vancomycin is a well-known glycopeptide antibiotic capable of strongly interacting with a broad range of Gram-positive bacteria. It interacts with bacterial cells through a surprisingly simple five-hydrogen bond motif between the heptapeptide backbone of vancomycin and the D-alanyl-D-alanine dipeptide extending from the cell wall. The interaction is quite strong with respect to small molecule_biomolecule interactions, with a dissociation constant (Kd) of about 1 to 4 micro Molar (M) at pH 7 similar to many antibody antigen interactions (Kd=1 micro Molar to about 1 fM). Though vancomycin offers less specificity/selectivity than monoclonal antibodies, it is very attractive as a ligand allowing affinity capture of a wide range of bacteria with a single vancomycin-functionalized particle.

The present disclosure relates in general to novel chemical entities comprised of multiple molecules of vancomycin which are covalently attached to a polyvinyl alcohol (PVA) backbone via carbodiimidizole chemistry (CDI). PVA is a water soluble, synthetic polymer with hydroxyl functions (—OH) attached to every other carbon. The general formula for PVA is —(CH2-CHOH)n- where "n" is the number of repeating units. Others have attempted to used CDI chemistry to attach primary amine-containing compounds to (m)Peg, but these reactions tend to merely "activate" the one (or two hydroxyls per molecule of (m)Peg in the present disclosure, the inventors have surprisingly and unexpectedly discovered composition and methods based on cdi-activation chemistry to activate most (if not all) of the hydroxyls on the PVA backbone. The methods and compositions described herein allow for multiple attachment points of any primary amine containing compounds in relatively close proximity to each other. In certain embodiments, the present disclosure relates to exemplary primary amines useful for coupling to the PVA backbone.

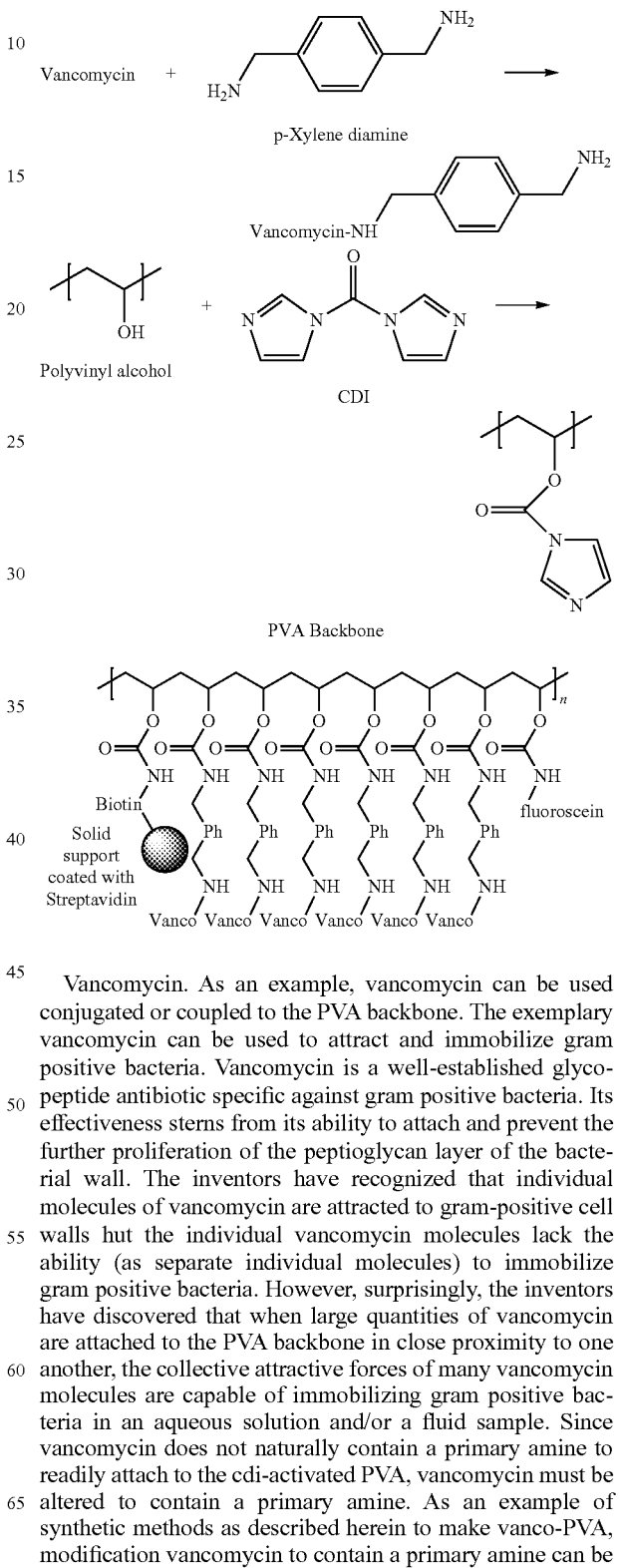

Vancomycin. As an example, vancomycin can be used conjugated or coupled to the PVA backbone. The exemplary vancomycin can be used to attract and immobilize gram positive bacteria. Vancomycin is a well-established glycopeptide antibiotic specific against gram positive bacteria. Its effectiveness stems from its ability to attach and prevent the further proliferation of the peptioglycan layer of the bacterial wall. The inventors have recognized that individual molecules of vancomycin are attracted to gram-positive cell walls hut the individual vancomycin molecules lack the ability (as separate individual molecules) to immobilize gram positive bacteria. However, surprisingly, the inventors have discovered that when large quantities of vancomycin are attached to the PVA backbone in close proximity to one another, the collective attractive forces of many vancomycin molecules are capable of immobilizing gram positive bacteria in an aqueous solution and/or a fluid sample. Since vancomycin does not naturally contain a primary amine to readily attach to the cdi-activated PVA, vancomycin must be altered to contain a primary amine. As an example of synthetic methods as described herein to make vanco-PVA, modification vancomycin to contain a primary amine can be accomplished by the conjugation with diaminoxylene (DAX) via HBTU chemistry, then followed by subsequent HPLC purification.

Biotin addition to PVA backbone. As an example, biotin is added in small quantities to the PVA backbone to serve as an anchoring point between the PVA compound and a solid support. Once biotin is attached to the PVA molecule, it can then facilitate the attachment of the PVA molecule to any solid support coated with streptavidin. An an example, EZ Link-PEO3-Biotin was used in this process, it is a pre-manufactured amine containing biotin molecule complete with a spacer arm (PEO3) to attach to the cdi-activated PVA.

Furthermore, in certain embodiments, a reporter molecule such as fluorescein, can be added in small quantities to the PVA backbone as a reporter to help "visualize" the attraction and capture of the bacteria in solution. In certain exemplary preparations, 5-(aminoacetamido) fluorescein can be used as an exemplary reporter, the use of this reagent provides a pre-manufactured amine containing flouroescein molecule to attach to the cdi-activated PVA.

As used herein, microorganism is understood to include any prokaryotic microscopic organism (including bacteria) or eukaryotic microscopic organism (including protozoa, algae, yeasts and fungi), and/or viruses. The bacteria can include those generally known as pathogenic bacteria, such as, for example, species of Enterobacteriaceae, Vibrionaceae, *bacillus Escherichia, Streptococcus, Pseudomonas, Salmonella, Legionella, Enterobacter*, etc. In some embodiments, the bacteria are gram negative bacteria. In other embodiments, the sample is gram positive bacteria.

As used herein, a support is understood to include a solid formed by a polymeric material which has, on its surface, a large number of chemical groups necessary for fixing molecules of interest.

As used herein, quantifying is understood as determining in an exact manner the concentration or amount of the microorganism of interest in the sample. Semi-quantifying is understood as determining in an approximate manner the concentration of the microorganism of interest in the sample. Detecting is understood as determining the presence-absence of the microorganism of interest in the sample.

As used herein, a "sample" includes any sample that is suspected of containing the microorganism. The sample will generally be of a diagnostic, environmental and/or food origin, and in certain cases will be of biological fluids.

As used herein, the term "selection" includes both "negative" selection and "positive" selection. Negative selection processes are processes in which the unwanted components are bound to the functionalized affinity separation particles are isolated during the procedure, leaving the desired components in the sample. On the other hand, "positive" selection processes include separation processes in which the wanted components are bound to the functionalized affinity separation particles and isolated during the procedure. In certain embodiments, separation processes are used to achieve an enrichment or the desired sample or depletion of the undesired sample.

As used herein, detection may involve, for example, fluorescence assay, enzyme-linked immunosorbent assay (ELISA), optical microscope, electron microscope, or a combination thereof.

In some embodiments, the biological test sample includes a biological fluid. Biological fluids are typically liquids at physiological temperatures and can include naturally occurring fluids present in, withdrawn from, expressed or otherwise extracted from a subject or biological source. Certain biological fluids derive from particular tissues, organs or localized regions and certain other biological fluids can be more globally or systemically situated in a subject or biological source. Non-limiting examples of biological fluids include blood, serum and serosal fluids, plasma, lymph, urine, cerebrospinal fluid, saliva, mucosal secretions of the secretory tissues and organs, vaginal secretions, breast milk, tears, and ascites fluids such as those associated with non-solid tumors-are also suitable. Additional examples include fluids of the pleural, pericardial, peritoneal, abdominal and other body cavities, and the like. Biological fluids can further include liquid solutions contacted with a subject or biological source, for example, cell and organ culture medium including cell or organ conditioned medium, lavage fluids and the like. In other embodiments the biological sample is blood serum, plasma, or the supernatant of centrifuged urine.

In certain embodiments, the capture of microbial samples such as bacteria sample can be achieved by coupling of vancomycin (e.g. effective for gram (+) bacteria) to the PVA. Moreover, the vanco-PVA compounds and compositions of this disclosure can be used in combination and/or coupled with other capture moieties, such as for example, polymyxin B, antilipid A, antigen, antiEcoli (pAb), lysozyme, deactivated lysozyme, ampicillin, anti-FLIC, cecropin, and bactenecin.

The present disclosure also provides a kit for the determination/detection/separation/concentration/purification of samples containing microorganisms. The scope of said determination/detection/separation/concentration/purification can be semiquantitative or quantitative; semiquantitative determination is understood as one in which the result is an estimation of the order of magnitude of the concentration of the microorganism of interest in the sample. The kit allows the selective capture of the microorganism of interest in aqueous, water and/or food samples, its concentration and separation from the remaining components of the sample, and its colorimetric detection, in a simple and rapid manner, in situ determination being possible. The kit uses vanco-PVA molecules directed against the microorganism of interest, immobilized on their surface, which in the supplied reaction media bind specifically to the microorganism of interest that is present or potentially present in the sample.

In one aspect, the disclosure provides a method of detecting microorganisms comprising steps of: (a) contacting a sufficient amount of vanco-PVA moiety with an appropriate sample for an appropriate period of time to permit the formation of complexes between the microorganisms and vanco-PVA complexes; (b) aggregate said complexes; and (c) detecting said complexes.

In one embodiment, the sensitivity of detection for the method can be at least as low as 10 colony forming units (cfu) of the microorganisms in one milliliter of solution. The exemplary method of the present invention is capable of detecting anywhere from about 20, 40, 60, 80, or 100 cfu/mL. In another embodiment, for viruses, the exemplary method of the present invention is capable of detecting concentrations at least as low as 10 plaque forming units per one milliliter of solution (pfu/mL) and upwards of about 100, 500, or 1000 pfu/mL.

In one embodiment, the microorganisms are pathogens. As used herein, pathogens are defined as any disease-producing microorganism. Pathogens include, but are not limited to, bacteria, viruses, mycoplasma, algae, amoeba, or other single-cell organisms. The bacteria may be either Gram positive or Gram negative, which may be captured and/or affinity separated. The bacteria can include, but are not limited to, *Staphylococcus aureus, Staphylococcus epi-*

*dermidis*, coagulase negative staphylococci (CNS), *E. coli*, or Vancomycin Resistant Enterococci (VRE).

The sample to be tested can be a clinical sample, which may include, but is not limited to, bodily fluid samples, smear samples, or swab samples. The sample can also be taken from the environment, which may include, but is not limited to, environmental sources such as water, air, or soil.

Additionally, the sample can be taken from food products, which may include, but is not limited to, liquid or solid foods that are processed, concentrated, or otherwise artificially modified. The present invention can be very beneficial to the food industry where sensitive detection of pathogens is desired. Samples, whether in solid, liquid, or gas form, can be prepared accordingly (e.g. dilution, dissolution, immersion) so as to render them in solution form for use in the present invention.

The solid supports useful in the compositions and methods of this disclosure include microsphere solid supports which may include protein microspheres or magnetic particles. In one embodiment, the protein microspheres, for example, albumin microspheres, such as human serum albumin microspheres. In some embodiments, the microspheres are unstabilized microspheres that have not been stabilized, for example by treatment with a cross-linking agent, tanning agent (such as Cr+++ or other alkali metal tanning agent), or a fixative (such as an aldehyde, e.g., glutaraldehyde or formaldehyde). In other embodiments, the microspheres may be stabilized. Microspheres which are unstabilized may advantageously be destroyed by solubilization with a detergent. The solid support particles may also be composed of magnetic spheres and bead, including but not limited to, polystyrene, or other polymeric or plastic microspheres, iron, noble metals (such as gold, silver, platinum, or palladium), cobalt, metal oxides, nickel, or alloys thereof. In one embodiment, the magnetic nanoparticles are iron-platinum (FePt), $SmCo_5$, $Fe_3O_4$, $Fe_2O_3$, FePd, CoPt, $Sm_xCo_y@Fe_2O_3$, $Sm_xCo_y@Fe_3O_4$, $M@Fe_2O_3$, or $M@Fe_3O_4$, whereby x=1 to 4, y=5 to 20, and M is a magnetic metal selected from the group consisting of cobalt, nickel, iron, and magnetic alloys thereof. In the embodiment described above involving $Sm_xCo_y@Fe_2O_3$, $Sm_xCo_y@Fe_3O_4$, $M@Fe_2O_3$, and $M@_3O_4$, the symbol "@" merely indicates that the magnetic nanoparticles have a $Sm_xCo_y$ or M core and a $Fe_2O_3$ or $Fe_3O_4$ shell. Metals which can be magnetic are well known in the art. See *Magnetic Nanoparticles Having Passivated Metallic Cores*. The functional group may be an antibiotic, ligand, receptor, or metal complex.

In another embodiment, after the bacteria has been captured by the vanco-PVA complex, a conjugate of Van and biotin (Van-Biotin) can be bound to the free D-Ala-D-Ala on the surface of the bacteria. This is beneficial, because the binding particles may not exhaust all the D-Ala-D-Ala (or other biomarkers) on the surface of the bacteria. Thus, the free D-Ala-D-Ala (or other biomarkers) are available for binding with a second ligand, a biotin conjugate such as Van-biotin. In some embodiments, a magnetic field can be used to aggregate the resulting complexes. By exploiting the interaction between biotin and avidin via an avidin-FITC (fluorescein isothiocyanate) conjugate, the presence of the bacteria can then be easily reported using conventional fluorescence or enzyme-linked immunosorbent assays (ELISA). Detection may further comprise analysis with an optical microscope, an electron microscope, or a combination thereof.

In one embodiment, the sample can be a biological sample selected from the group consisting of blood, serum, serosal fluid, plasma, lymph, urine, cerebrospinal fluid, saliva, a mucosal secretion, a vaginal secretion, ascites fluid, pleural fluid, pericardial fluid, peritoneal fluid, abdominal fluid, culture medium, conditioned culture medium and lavage The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The vanco-PVA may be immobilized on the solid support using a variety of techniques known to those in the art, which are amply described in the patent and scientific literature.

In certain embodiments, the vanco-PVA complex can contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of antibody remaining on the support after wash. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (by way of example, see Scouten, W. H. (1987) A survey of enzyme coupling techniques. Methods in. Enzymology 135, 30-65). Spectroscopic method can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well-known techniques.

Standard recombinant DNA and molecular cloning techniques used in the examples are well known in the art.

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

EXAMPLES

Prior to the experiments described herein, there was no published protocol that allows for optimal separation of gram positive or gram negative microorganisms with a PVA conjugated vancomycin, biotin and/or fluorescein complex. Aspects and embodiments of the instant disclosure stem from the unexpected discovery that PVA conjugated vancomycin, fluorescein and biotin complex have surprising and unexpected utility and efficacy when used for capture, separation, and/or isolation of microorganisms.

In the experiments described herein, several factors were discovered that allowed for the unexpected enhanced/potentiated efficacy in the synthesis and/or use of the PVA vancomycin complex. For example, it was discovered that when large quantities of vancomycin are attached to the PVA backbone in close proximity to one another, the collective attractive force of many vancomycin molecules are capable of immoblizing grain positive/(and/or negative bacteria in solution. It was discovered that multiple molecules of vancomycin can be covalently attached to a polyvinyl alcohol (PVA) backbone via a modified carbodiimidizole (CDI) chemistry reaction that can activate most (if not all) of the hydroxyls on the PVA. backbone. This allows multiple attachment points of any primary amine containing compounds in relatively close proximity to each other.

By way of example, methods for synthesizing PVA backbone with Vancomycin, biotin, and/or fluorescein conjugates were developed.

Example 1

Preparation of Vancomycin/Diaminoxylene (DAX) Conjugate

HPLC purified vancomycin-DAX

First, 300 mg, 274 mg, 115 mg and 78 mgs of Vancomycin hydrochloride (MW of 1485.74 g/mole, 202 umoles), p-xylene diamine (MW of 136.2 g/mole, 2020 umoles), HBTU (2-(1h-benzotriazol-1-yl)-1,1,3,3,-tetramethyluronium hexafluorophosphate MW of 379.3 g/mole, 303 umoles), and N,N disopropyl ethylamine(MW of 129.24 g/mole, 606 umoles) were dissolved in 1500 ul of DMSO, 1500 ul of DMF, HBTU (provided in 0.500 molar solution) (catalog #401091 lot #EG083 from Applied Biosystems), and as a neat solution respectively. Next, 200 uls of vancomycin hydrochloride solution was placed in a 1 ml vial, followed by 90 microlilters of HBTU solution and 13 microliters of DIEA (used neat reagent of 107 microliters), the resulting solution was stirred for 10 minutes. This mixture was then transferred to a separate vial containing 200 ul of DAX. The mixture was stirred for one hour at room temperature followed by HPLC purification using the Hamilton 5 u silica 7 mm×300 mm column and an Agilent 5 u C-18 4×250 mm column. The resultant HPLC purified vancomycin-DAX was obtained.

Preparation of 1 mg/mL, PVA 5.50 mg, 8.68 mg, and 3.92 mg of high—(89,000-98,000 typical MW, 99+% hydrolyzed), mid—(31,000-50,000 typical MW, 99% hydrolyzed), and low—(13,000-23,000 typical MW, 98% hydrolyzed) molecular weight PVA [Sigma-Aldrich] were placed in separate 5 mL glass tubing vials respectively. Corresponding quantities (5.50 mL, 8.68 mL, and 3.92 mL) of anhydrous Dimethyl Sulfoxide (DMSO) [Sigma-Aldrich] was added to each tubing vial, then sealed with Teflon-coated rubber stoppers and a crimped aluminum overseal. The tubing vials were repeatedly vortexed and then heated to 60° C. until all the powdered PVA had dissolved in all solutions.

To make room for the addition of molecular sieves, half (4.34 mL) of the mid-MW PVA solution was removed from that tubing vial and discarded. Approximately 5 mL of molecular sieves [3A, 1.6 mm Sigma-Aldrich] was added to each tubing vial. The tubing vials were then re-sealed, capped, then mounted on a rotation wheel and rotated slowly overnight to remove any residual water contained in the DMSO or PVA, Activation of PVA with CDI at 10× Molar Excess (Over Available Hydroxyls)

First, 34.9 mg, 40.5 mg, and 38.9 mg of 1,1-Carbonyl-diimidazole (CDI) [Sigma-Aldrich] were respectively placed in separate 5 mL glass Reacti-vials [Pierce] fitted with Teflon-coated Reacti-vial magnetic stirrers [Pierce] and sealed with Tuf-bond Teflon/silicone disc septums [Pierce].

Each Reacti-vial was then purged with Argon [Airgas] at approximately 90 cc/min for at least (NLT) 2 minutes by means of piercing the septum with a 22G needle, plumbed to the Ar gas line, and vented with a separate 22G needle. The purge needle was placed as close to the powder at the bottom of the Reacti-vial without actually disturbing it. The purge needle was placed as close to the septum (top of the vial) as possible. These needle positions optimize the amount of moisture and air eliminated from the Reacti-vial without disturbing the powder.

Then, 1 mL (1 mg) each of high-, mid-, and low-MW anhydrous PVA was added to each of the Reacti-vials via gas-tight syringe. The Reacti-vials were instantly vortexed, then purged with Ar for NLT 2 minutes, then placed on a magnetic stir plate to mix overnight.

Vancomycin, Fluorescein, and Biotin conjugates at 0.9×, 0.28×, and 0.2.8× molar excess (over available hydroxyls), were added respectively.

6.53 mg of Vancomycin/DAX, 0.47 mg of 5-(aminoacetamido) Fluorescein [Invitrogen], and 0.51 mg EZ Link Biotin-PEO$_3$-Amine [Pierce] were transferred into a virgin 5 mL Reacti-vial. The Reacti-vial was sealed and purged with Ar as previously described. 300 µL of aDMSO was added to the Reacti-vial via air-tight syringe, then vortexed until all powder constituents were dissolved in solution.

3 empty Reacti-vials were sealed, then purged with Ar. 100 µL of vancomycin/fluorescein/biotin/DMSO was transferred via air-tight syringe into each vial. Then 65 µL (0.065mg) of cdi-activated high-, mid-, or PVA was each added to the vials. Each Reacti-vial was immediately vortexed, wrapped in aluminum foil, then mounted on a rotation wheel and rotated slowly overnight to allow the vancomycin, Fluorescein, and biotin to react with the CDI activated PVA.

Preparation of a PVA Control (Biotin Conjugation Only)

13.55 mg Biotin-PEO$_3$-Amine was dissolved in 100 µL anhydrous DMSO, the sample was then vortexed until the powder was dissolved in the solution. All 100 µL of Biotin/DMSO along with 1 µL of mid-MW cdi-activated PVA (excess previously made above), and 1 mL of anhydrous DMSO were all added to a virgin 5 mL glass Reacti-vial. A Reacti-vial magnetic stirrer was inserted into the glass Reacti-vial, then the vessel was sealed with a Tuf-Bond Teflon/silicone disc septum. The Reacti-vial was then purged with Ar for NLT 2 minutes as previously described. The Reacti-vial was stirred overnight to allow the biotin to react with the CDI-active PVA.

Example 2

Capture of m/o+ with PVA/(v)ancomycin/(f)luorescein/(b)iotin

Immoblize PVA/v/f/b onto Magnetic Particles

100 µL of Biomag Streptavidin particles [xxx] was transferred into a polypropylene (PP) centrifuge tube and was washed 3-times by the application of a strong magnetic field, removal of the liquid phase, and resuspension of the magnetic particles in 100 µL of PBS under vortex. This solution was then divided among 8 new PP centrifuge tubes transferring 10 µL of washed magnetic particles into each centrifuge tube.

1 µL of the high-MW PVA/v/f/b was added to tube #01 and tube #02.

1 µL of the mid-MW RVA/v/f/b was added to tube #03 and tube #04.

1 µL of the low-MW PVA/v/f/b was added to tube #05 and tube #06.

1 µL of the control PVA/b was added to tube #07 and tube #08.

Each tube was then vortexed and allowed to incubate for 30 minutes to allow the streptavidin coated magnetic particles to bind to the biotin active sites of the PVA, Preparation of $5 \times 10^4$ cell/mL Gram Negative bacteria Cultures of *Staphylococcus epidermidis* and *Streptococcus gallolyticus* were initiated from known colony plates and incubated in LB broth [IPM Scientific] at 37° C. overnight. 1 mL of each bacterial solution was transferred into separate plastic disposeable cuvettes and placed in a spectrophotometer [Uvikon 933, Kontron hidustries]. The absorbance of both solutions was measured at 600 nm with LB broth as the reference (zero) standard and found to be 0.326 and 0.283, respectively. Assuming that the cell density is approximately equal to the OD reading$\times 10^9$, the cell solutions were diluted with PBS to obtain a final cell density of approximately $5 \times 104$ cells/mL. Thus, 0.767 µL of *S. epidermidis* was added to 5 mL of PBS and 0.884 µL of *S. gallolyticus* was added to 5 mL of PBS.

Addition of $5 \times 10^4$ cell/mL Bacteria to Immobilized PVA

100 µL×4 of *S. epidermidis* was added to tube #01, #03, #05, and #07.

100 µL×4 of *S. gallolyticus* was added to tube #02, #04, #06, and #08.

Each tube was vortexed and allowed to incubate for 1 hour at room temperature.

Propagation of Bacteria

A strong magnetic field was applied to each centrifuge tube until all of the magnetic particles migrated to one side. With the magnetic field still applied, 10 µL of liquid (no mag particles) was extracted from each centrifuge tube and transferred onto separate LB agar plates [IPM Scientific]. The liquid on the agar plates were then streaked to distribute the liquid evenly across the entire surface of the plate. The plates were then incubated at 37° C. overnight to allow any colony forming units (CFUs) to proliferate.

With the magnetic field still applied, the remaining liquid was removed from each centrifuge tube and discarded. Then, with the magnetic field removed, 10 µL of PBS was added to each centrifuge tube and vortexed to resuspend the magnetic particles. All 10 µL of magnetic particles were then transferred onto LB agar plates and streaked to distribute the liquid evenly across the entire surface of the plate. The plates were then incubated at 37° C. overnight to allow any colony forming units (CPUs) to proliferate.

All agar plates were removed from incubation and visually inspected for the presence of CFUs. CFUs (if present) were counted and recorded. Results of each agar plate count are tabulated below:

| Sample | Bacteria | PVA MW | CFU (liquid) | CFU (immobilized) |
|---|---|---|---|---|
| Tube #01 | S. epidermidis | High | 0 | 300+ |
| Tube #02 | S. gallolyticus | High | 0 | 62 |
| Tube #03 | S. epidermidis | Mid | 0 | 300+ |
| Tube #04 | S. gallolyticus | Mid | 0 | 25 |
| Tube #05 | S. epidermidis | Low | 0 | 200+ |
| Tube #06 | S. gallolyticus | Low | 0 | 56 |
| Tube #07 | S. epidermidis | Control | 18 | 79 |
| Tube #08 | S. gallolyticus | Control | 9 | 07 |

From the table above, it is readily apparent that when vancomycin is conjugated to any PVA backbone and immobilized on a solid support, that all bacteria are captured by that solid support. The capture efficiency appears to be 100% as all bacteria are associated with the magnetic particles (solid support) and none remain in the surrounding liquid.

Also, because magnetic particles can efficiently be separated from their surrounding liquid, this mechanism of capture would allow for the concentration of bacteria in solution. 1% (or less) concentrations of magnetic particles in solution would result in a minimum of 2 orders of magnitude concentration factors for the bacteria.

Thus, vancomycin conjugated on a PVA backbone and immobilized on a solid support is capable of capturing and concentrating gram positive/negative bacteria in solution.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A synthetic polymer comprising repeating monomer units of polyvinyl alcohol
    wherein each hydroxyl group is covalently bound to a molecule of carbonyldiimidazole,
    wherein a first population of the monomeric units each comprises a linker covalently bound to the carbonyldiimidazole and a solid support,
    wherein a second population of the monomeric units each comprises activated vancomycin, and
    wherein optionally a third population of the second monomeric units each comprises a fluorescent molecule.

2. The synthetic polymer of claim 1, wherein the second population comprise more monomeric units as compared to the first or the third population.

3. The synthetic polymer of claim 1, wherein the activated vancomycin is bound to the second population of the monomeric units through para-xylene diamine.

4. The synthetic polymer of claim 1, wherein the synthetic polymer has the general formula (I):

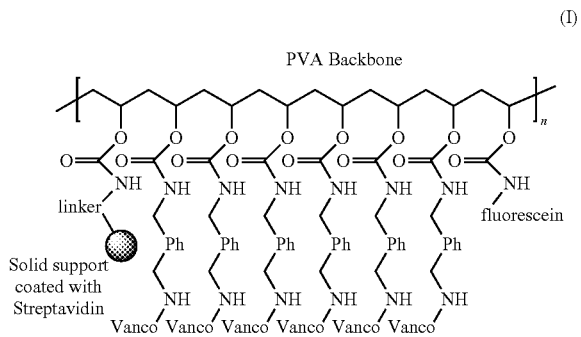

(I)

wherein the linker is biotin.

5. The synthetic polymer of claim 2, wherein the second population comprise at least 10 fold excess of monomeric units as compared to the first population or the third population.

6. The synthetic polymer of claim 1, wherein the solid support comprises a magnetized particle.

7. The synthetic polymer of claim 1, wherein the magnetized particle is coated with streptavidin.

8. The synthetic polymer of claim 1, wherein the fluorescent molecule is 5-(aminoacetamido) fluorescein.

9. A method for capturing, detecting, concentrating, or depleting microorganisms in a test sample, the method comprising:
   a) adding a synthetic polymer comprising repeating monomer units of polyvinyl alcohol wherein each hydroxyl group is covalently bound to a molecule of carbonyldiimidazole, wherein a first population of the monomeric units each comprises a linker covalently bound to the carbonyldiimidazole and a solid support, and wherein a second population of the monomeric units each comprises activated vancomycin, and wherein optionally a third population of the monomeric units each comprises a fluorescent molecule to a solution comprising the microorganisms to form a mixture;
   b) agitating the mixture from step a) followed by incubation, wherein the synthetic polymer form complexes with the microorganisms;
   c) separating the complexes from the mixture from step b); and
   d) detecting, capturing, concentrating, or depleting the microorganisms that are bound to the synthetic polymer.

10. The method of claim 9, wherein the complexes formed by the synthetic polymer and microorganisms comprise an affinity molecule selected from the group consisting of: a receptor, a ligand, an antibody, a hormone, RNA, DNA, PNA or nucleotide derivatives or analogs, biotin, avidin, and streptavidin.

11. The method of claim 9, wherein the microorganisms are bacteria.

12. The method of claim 9, wherein the microorganisms are gram positive or negative bacteria.

13. The method of claim 9, wherein the microorganisms are selected from *Staphylococcus epidermidis* and *Streptococcus gallolyticus*.

14. The method claim 11, wherein the bacteria are *Staphylococcus*.

15. The method of claim 9, wherein the synthetic polymer comprises a polyvinyl alcohol backbone, wherein the polyvinyl alcohol backbone is conjugated to primary amine containing vancomycin produced by diaminoxylene (DAX) using HBTU chemistry.

16. The method of claim 9, wherein the synthetic polymer comprises a polyvinyl alcohol backbone, wherein the polyvinyl alcohol backbone is conjugated to avidin.

17. The method of claim 9, wherein the synthetic polymer comprises a polyvinyl alcohol backbone, wherein the polyvinyl alcohol backbone conjugated to polymyxin B; anti-lipid A; antigen; antiEcoli (pAb); lysozyme; deactivated lysozyme; ampicillin; anti-FLIC; cecropin; or bactenecin.

18. The method of claim 9, wherein the synthetic polymer comprises a polyvinyl alcohol backbone, wherein the polyvinyl alcohol backbone is conjugated to a fluorescent molecule.

19. The method of claim 9, wherein the sample is a liquid selected from blood, serum, plasma, spinal fluid, synovial fluid, saliva, urine, semen, cell and/or tissue homogenates.

20. A process for preparing a synthetic polymer of general formula (I)

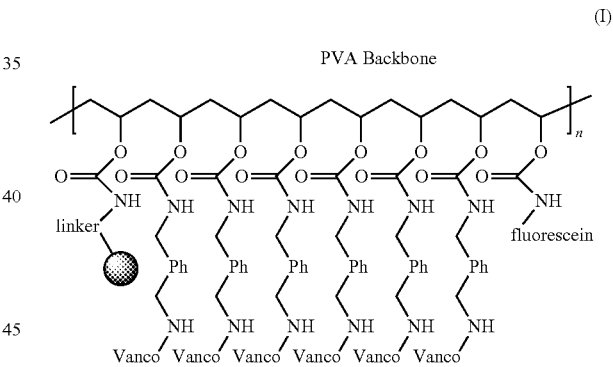

(I)

wherein n is 10 to 100, comprising the steps:

a) reacting vancomycin with para-xylene diamine to give the compound of formula (II):

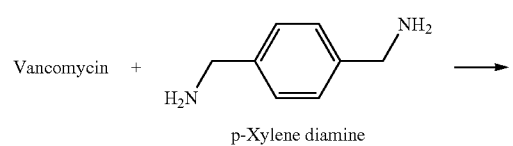

-continued

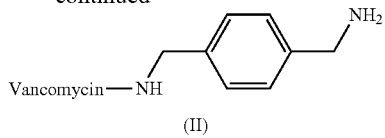

(II)

b) reacting polyvinyl alcohol with a molar excess of carbonyldiimidazole to give the compound of formula (III):

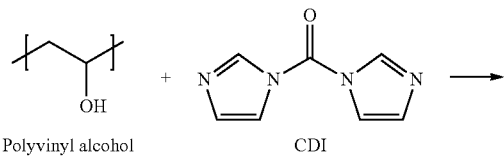

Polyvinyl alcohol          CDI

(III)

c) reacting the compound of formula (II) from step a), the compound of formula (III) from step b), a linker, and optionally, a fluorescent molecule to give a compound of formula (IV); and (IV)

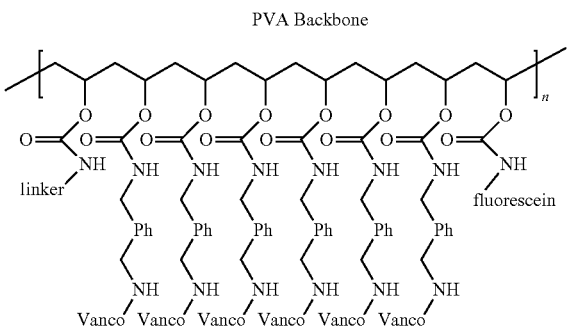

d) reacting the compound of formula (IV) from step c) with a solid support to produce synthetic polymer (I).

21. The process of claim 20, wherein the carbonyldiimidazole is used in a molar excess from about 5 to about 15.

22. The process of claim 20, wherein the fluorescent molecule is 5-(aminoacetamido) fluorescein.

23. A kit comprising the polymer of claim 1 and instructions for use.

24. The method of claim 9, wherein the detecting the microorganisms that are bound to the synthetic polymer further comprises
   i) transferring the polymer from step d) to agar plates to allow any colony forming units to proliferated; and
   ii) visually inspecting the agar plates from step e) for the presence of any colony forming units.

* * * * *